United States Patent
Runft et al.

(10) Patent No.: US 9,042,515 B2
(45) Date of Patent: May 26, 2015

(54) DEVICE FOR CHECKING PHARMACEUTICAL PRODUCTS, IN PARTICULAR HARD GELATIN CAPSULES

(75) Inventors: Werner Runft, Winnenden (DE); Iulian Maga, Ludwigsburg (DE); Jens Schlipf, Freiberg A. N. (DE); Martin Vogt, Schomdorf (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 14/111,742

(22) PCT Filed: Mar. 1, 2012

(86) PCT No.: PCT/EP2012/053556
§ 371 (c)(1),
(2), (4) Date: Oct. 14, 2013

(87) PCT Pub. No.: WO2012/139811
PCT Pub. Date: Oct. 18, 2012

(65) Prior Publication Data
US 2014/0050299 A1  Feb. 20, 2014

(30) Foreign Application Priority Data

Apr. 13, 2011  (DE) .......................... 10 2011 007 277

(51) Int. Cl.
*G01N 23/083*  (2006.01)
*G01N 23/10*  (2006.01)
(Continued)

(52) U.S. Cl.
CPC  *G01N 23/02* (2013.01); *G01T 7/08* (2013.01); *G01N 33/15* (2013.01); *G01T 7/10* (2013.01);
(Continued)

(58) Field of Classification Search
CPC .............. G01T 7/00; G01T 7/08; G01T 7/10; H01J 37/20; G01N 33/15
USPC ........ 378/51–56, 62, 204, 208, 210; 250/304, 250/306, 307, 308, 440.11, 441.11, 442.11, 250/589, 590, 453.11, 491.1, 526; 209/539–541, 544, 545, 589, 684–690, 209/909; 198/392, 469.1, 470.1, 474.1, 198/476.1, 478.1, 479.1, 480.1, 481.1, 48, 198/2.1, 608, 611–613

See application file for complete search history.

(56) References Cited

U.S. PATENT DOCUMENTS 2,339,115 A  *  1/1944  Scherer ........................... 53/473
2,630,953 A  *  3/1953  Kath ............................... 53/281
(Continued)

FOREIGN PATENT DOCUMENTS

CN  1854722  11/2006
CN  1956695  5/2007
(Continued)

OTHER PUBLICATIONS

International Search Report for Application No. PCT/EP2012/053556 dated Aug. 31, 2012 (2 pages).

*Primary Examiner* — Anastasia Midkiff
(74) *Attorney, Agent, or Firm* — Michael Best & Friedrich LLP

(57) ABSTRACT

The invention relates to a device (10; 10a;10b; 10c; 50) for checking pharmaceutical products (1), in particular hard gelatin capsules, by means of at least one radiation source (30; 60) preferably embodied as an X-ray source, and a conveying device which conveys the products (1) in a clocked manner in a radiation area (31) of the radiation source (30; 60). The radiation emitted by the radiation source (30; 60) penetrating the products (1) preferably perpendicular to the longitudinal axes thereof (2), and the radiation is captured on the side of the products (1) opposite the radiation source (30) by means of at least one sensor element (35) which is coupled to an evaluation device (36). The invention is characterized in that the conveyor device is embodied as a conveyor wheel (15; 15a; 51) which can rotate in a stepped manner about an axis (12; 52), and the products (1) are arranged, while being conveyed in the radiation area (31), in receiving areas (28; 37; 56) of the conveyor wheel (15; 5a; 51).

25 Claims, 7 Drawing Sheets

(51) Int. Cl.
  *G01N 33/15*  (2006.01)
  *H05G 1/02*  (2006.01)
  *G01N 23/02*  (2006.01)
  *G01T 7/08*  (2006.01)
  *G01T 7/10*  (2006.01)
  *G01N 23/04*  (2006.01)
  *A61J 3/07*  (2006.01)
  *G01N 15/00*  (2006.01)
  *G01N 35/00*  (2006.01)
  *G01N 15/14*  (2006.01)

(52) U.S. Cl.
  CPC ............... *A61J 3/074* (2013.01); *G01N 23/043* (2013.01); *G01N 2223/633* (2013.01); *G01N 2223/652* (2013.01); *G01N 2015/0019* (2013.01); *G01N 2035/00564* (2013.01); *G01N 15/1459* (2013.01)

(56) References Cited

U.S. PATENT DOCUMENTS

| | | | |
|---|---|---|---|
| 3,493,746 A | 2/1970 | Webb | |
| 4,144,970 A * | 3/1979 | McKnight et al. | 209/542 |
| 7,012,242 B2 * | 3/2006 | Tarozzi et al. | 250/222.1 |
| 7,792,247 B2 * | 9/2010 | Schmied et al. | 378/54 |

FOREIGN PATENT DOCUMENTS

| | | |
|---|---|---|
| CN | 2920242 | 7/2007 |
| DE | 102010038544 | 4/2011 |
| WO | 2006027793 | 3/2006 |
| WO | 2006106012 | 10/2006 |

* cited by examiner

DEVICE FOR CHECKING PHARMACEUTICAL PRODUCTS, IN PARTICULAR HARD GELATIN CAPSULES

BACKGROUND OF THE INVENTION

The invention relates to a device for checking pharmaceutical products, in particular hard gelatin capsules.

Such a device is known from the post-published German patent application DE 10 2010 038 of the applicant. In the known device, a conveyor wheel which is disposed about a vertical axis of rotation and is rotated in a stepped manner is provided in one embodiment. Receiving segments having receiving bores for receiving respectively one hard gelatin capsule are exchangeably attached on the circumference of said conveyor wheel. In order to check the hard gelatin capsules in the region of an X-ray source, the hard gelatin capsules are pushed by means of receiving plungers out of the receiving bores of the receiving segments over into the region of a sensor device disposed above the receiving segments. A shaft-shaped conveyor element then serves to guide the hard gelatin capsules in the region of the sensor device. Before the hard gelatin capsules are pushed into the receiving bores of the receiving segments, said capsules are disposed in a bulk storage unit, e.g. in the form of a storage container. Two transfer processes are therefore required for the hard gelatin capsules prior to being irradiated by the X-ray source. The hard gelatin capsules are initially pushed out of the bulk storage unit and inserted or, respectively, sorted into the receiving bores of the receiving segments, and said hard gelatin capsules are subsequently pushed out of the receiving bores of the receiving segments into the region of the sensor device. Such a handling of said hard gelatin capsules is relatively cumbersome and incurs the risk of damaging said capsules.

SUMMARY OF THE INVENTION

In light of the prior art described above, it is the aim of the present invention to facilitate a simplified handling of the products, which particularly transports the pharmaceutical products more gently into the region of the sensor device. Furthermore, performance and output are to be increased with respect to the prior art.

This aim is met according to the invention by a device for checking pharmaceutical products, in particular hard gelatin capsules, by virtue of the fact that the conveying device is embodied as a conveyor wheel which can rotate in a stepped manner about an axis and by virtue of the fact that the products are arranged, whilst being conveyed in the radiation area, in receiving areas of the conveyor wheel. By means of the inventive embodiment of the device, it is therefore no longer necessary to remove the products from the receiving areas of the conveyor wheel in order to expose said products to radiation. In contrast thereto, said products are exposed to radiation or, respectively, irradiated during the transport thereof when the device is in a standstill phase. In so doing, not only the complexity of handling is reduced for the device with respect to the prior art but the possibility also results to increase the performance of said device because only a single conveying operation, loading the receiving areas of the conveyor wheel with products, has to be taken into account.

Provision is made in a first structural embodiment of the device for the conveyor wheel to comprise a stationary inner ring which forms a support surface for the products and is radially enclosed by an outer ring, for the receiving areas, preferably in the form of apertures, to be configured in the outer ring and for said outer ring to be rotationally mounted.

In order to prevent the products from falling out of the receiving areas when the conveyor wheel is rotated about the horizontally arranged axis of rotation thereof, provision is thereby made in a further embodiment of the invention for the outer ring to be enclosed by a protective cover at least in the region of the receiving areas.

In order to achieve a selective guidance of the products while being conveyed in the conveyor wheel and thereby reduce the danger of damage to said products, provision is made in a further structural configuration for the inner ring to have guide grooves for the products.

Provision is made in a very preferred embodiment of the invention for the receiving areas to have an extension in the direction of rotation which is greater than the extension of the products in the direction of transportation, for the radiation area of the radiation source to be disposed in a region of the conveyor wheel in which the products are prevented from moving independently in the direction of transportation by the frictional force between the products and the receiving surface of the inner ring, and for the outer ring to be rotatable in and counter to the direction of transportation. By means of this embodiment, it is now possible to release the products to be irradiated from the receiving areas by moving the outer ring backwards a small distance after said products are situated in the radiation cone. In so doing, interferences for the radiation source caused by the outer ring are particularly minimized.

In a fundamentally different structural embodiment of the invention, provision is made for the conveyor wheel to be mounted in a vertical axis of rotation and for vertically disposed receiving bores for the products to be configured in said conveyor wheel. Such an arrangement substantially corresponds to the configuration of the conveyor wheel in the German patent application DE 10 2010 038 544 A1 with the exception that the products are X-rayed or, respectively, irradiated within the conveyor wheel in the case of the device according to the invention.

In order to be able to use the conveyor wheel for different product formats, provision is preferably made for the receiving bores to be disposed in formatting portions which are exchangeably attached to said conveyor wheel. In order to improve performance, provision can thereby be made for each formatting portion to have a plurality of receiving bores.

In order to be able to X-ray or irradiate the products within the conveyor wheel, it is important that the formatting portion (for receiving the products) consists of a material that is permeable to the radiation from the radiation source. Plastic is, for example, one such material. In addition, formatting portions made from plastic can also be produced relatively simply and cost effectively.

Provision is made in a further option to increase performance for a plurality of products to be vertically disposed one above the other in the receiving bore.

BRIEF DESCRIPTION OF THE DRAWINGS

Further advantages, features and details of the invention ensue from the following description of preferred exemplary embodiments as well as with the aid of the drawings. In the drawings.

DETAILED DESCRIPTION

Figure 1:
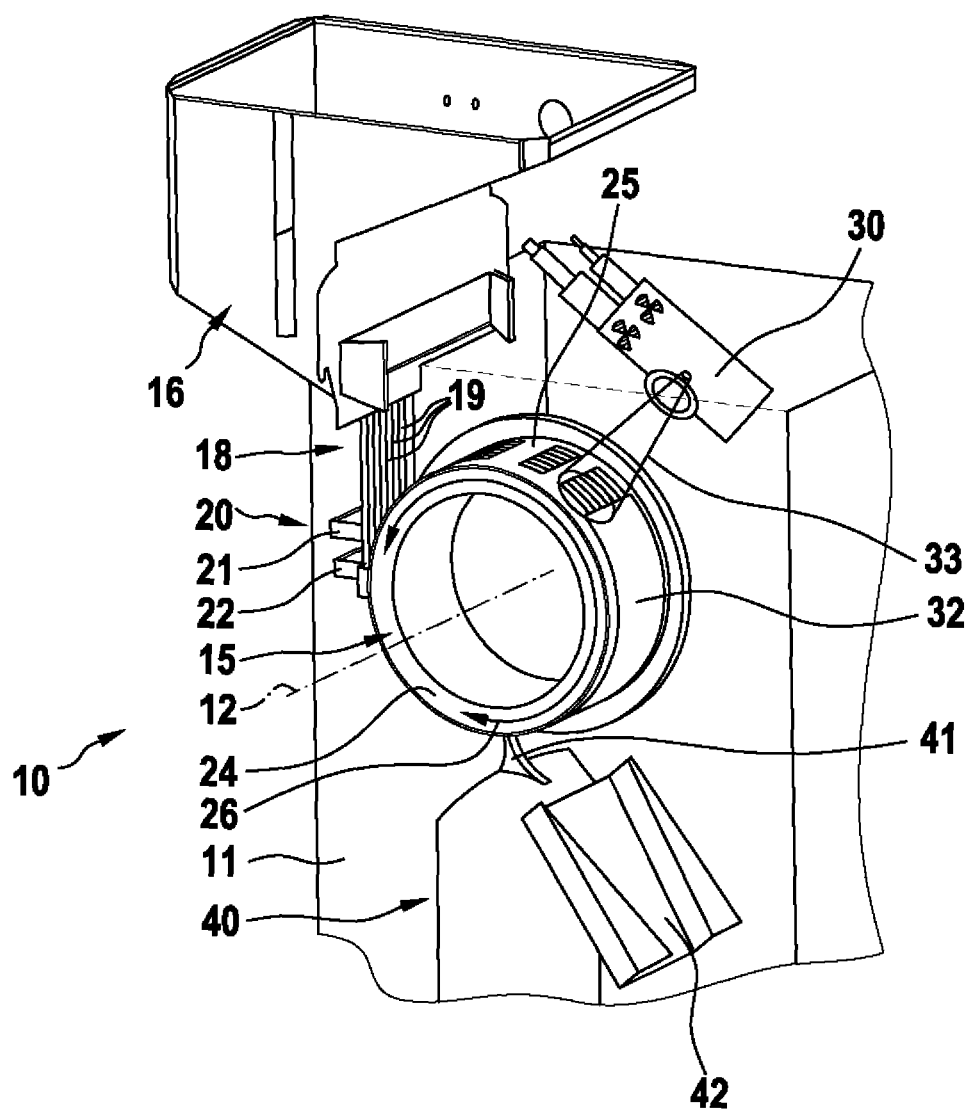
FIG. 1 shows a first inventive device for checking pharmaceutical products in a simplified perspective depiction.

The same components or components having the same function are denoted in the figures with the same reference numerals.

Figure 2:
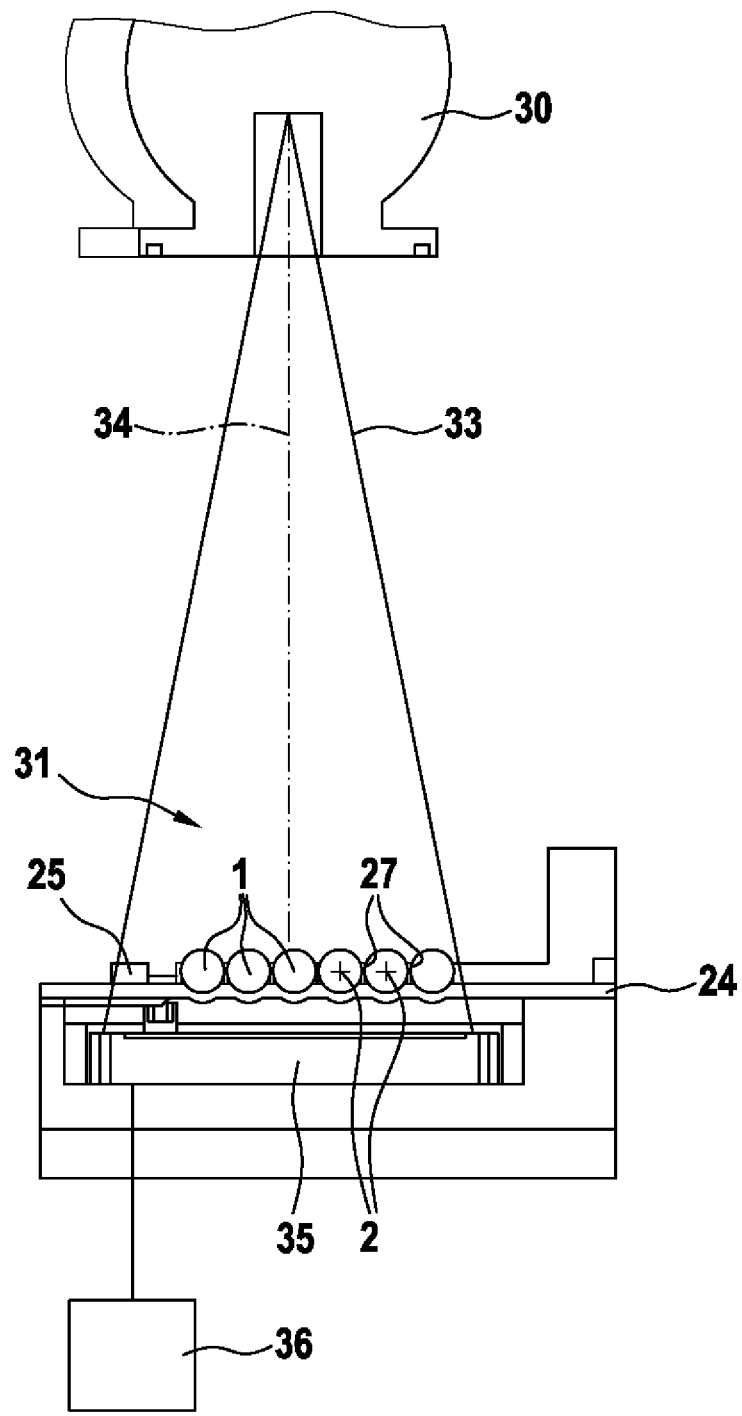
FIG. 2 shows in detail a portion of FIG. 1 in the region of the X-ray source in a partial cross-section.
Figure 3:
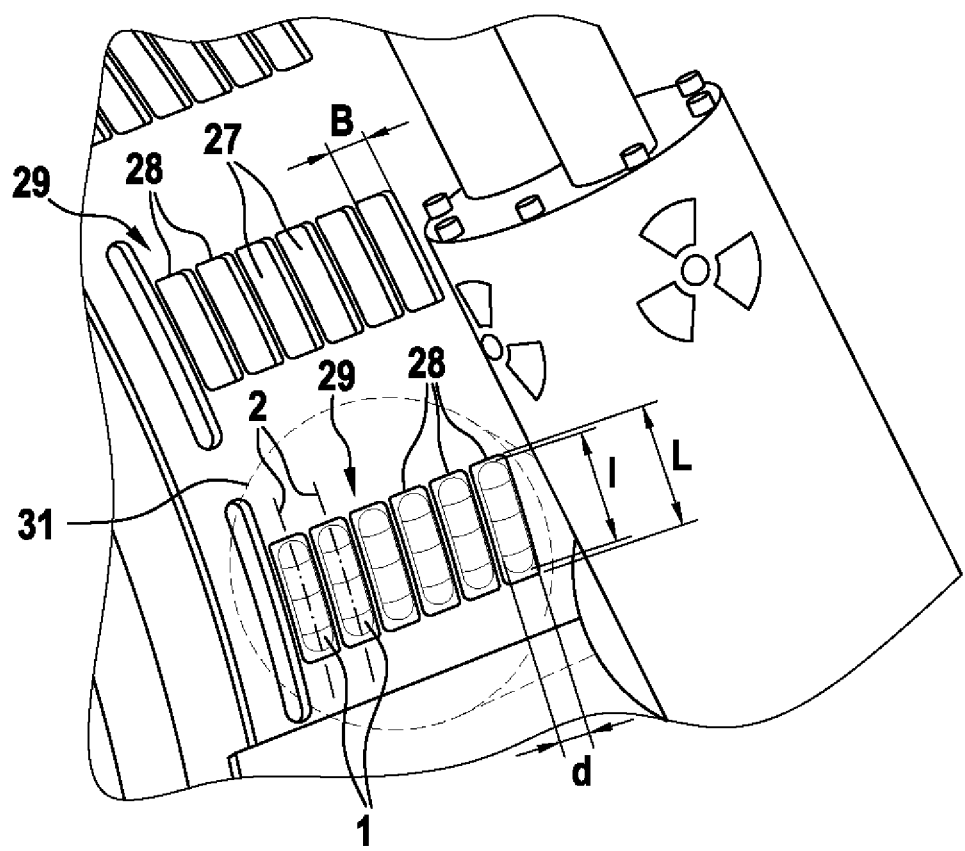
FIG. 3 shows the portion shown in detail pursuant to FIG. 2 in a perspective view.

A first inventive device 10 for checking pharmaceutical products, in particular hard gelatin capsules 1 (see FIGS. 2 and 3), is depicted in FIGS. 1 to 3. In this regard, checking hard gelatin capsules 1 or, respectively, pharmaceutical products refers particularly to checking the same for a correct filling weight as well as checking for the presence of (undesirable) foreign particles in the case of hard gelatin capsules 1.

The device 10 comprises a machine frame 11 out of the front wall of which, a conveyor wheel 15 protrudes, which is rotated in a stepped manner about a horizontal axis of rotation 12 by means of a drive (not depicted), in particular by means of a servodrive. A bulk storage unit 16 for the hard gelatin capsules 1 in the shape of a funnel is disposed laterally above the conveyor wheel 15. A feeding magazine 18, which is adapted to the format of the hard gelatin capsules and has a plurality of receiving shafts 19 that are vertically aligned to the axis of rotation 12, is located between the bulk storage unit 16 and the conveyor wheel 15. The hard gelatin capsules 1 situated irregularly in the bulk storage unit 16 are disposed in the receiving shafts 19 in the form of hard gelatin capsules 1 which stand in each case as a row one above the other. In so doing, the feeding of said hard gelatin capsules 1 from the bulk storage unit 16 into the receiving shafts 19 of the feeding magazine 18 takes place in a known manner, for example by means of vibration or an intermittent reciprocal movement.

A blocking device 20 is disposed at the lower end of the feeding magazine 18, which end faces away from the bulk storage unit 16. The blocking device 20 has, for example, two blocking plungers 21, 22, which can be moved into and out of the region of the individual receiving shafts 19 of the feeding magazine 18, or something similar. By means of the blocking device 20, at least the respectively lowest hard gelatin capsules 1 can be conveyed or channeled out of the receiving shafts 19 into the region of the conveyor wheel 15.

The conveyor wheel 15 has, as can particularly be seen when considering FIGS. 1 and 3 together, a stationary inner ring 24 that forms a support surface for the hard gelatin capsules 1 and an outer ring 25 which radially encompasses the inner ring 24 and can be rotated with respect to said stationary inner ring 24. The outer ring 25 is rotated by means of an unspecified drive in accordance with the double arrow 26 in both a clockwise and counterclockwise manner. On the outer peripheral surface thereof and corresponding to the number of receiving shafts 19, the inner ring 24 has a guide groove 27 for each receiving shaft 19, said guide groove extending in the circumferential direction. This can particularly be seen with the aid of FIGS. 2 and 3. The guide grooves 27 serve to receive the hard gelatin capsules 1 in a partially positive locking manner and cause the longitudinal axes 2 of the hard gelatin capsules 1 to align with the guide grooves 27 during transport of said hard gelatin capsules 1.

The outer ring 25 is radially spaced apart from the inner ring 24. The outer ring 25 has a plurality of receiving areas for the hard gelatin capsules 1 in the shape of elongated apertures 28 which are aligned flush with the guide grooves 27. In so doing, a number of apertures 28 corresponding to the number of guide grooves 27 or, respectively, receiving shafts 19 is combined in each case to form a group 29 of apertures 28, wherein the apertures 28 belonging to a group 29 are disposed next to or behind each other in the direction of the axis of rotation 12 of the outer ring 25, as can particularly be seen with the aid of FIG. 3. A plurality of groups 29 of apertures 28 is furthermore disposed over the circumference of the outer ring 25 preferably in each case at uniform angular spacings. The apertures 28 on the outer ring 25 serve to entrain the hard gelatin capsules 1 disposed in the guide grooves 27, wherein the radial distance between the inner ring 24, more precisely stated between the guide grooves 27, and the outer ring 25 is smaller than the thickness d of the hard gelatin capsules 1. The length L of an aperture 28 is preferably greater in the direction of transportation or, respectively, the direction of rotation than the length l of a hard gelatin capsule 1 or the total length of the hard gelatin capsules 1 if multiple hard gelatin capsules 1 are simultaneously disposed in an aperture 28 of the outer ring 25. The width B of an aperture is preferably somewhat wider than the thickness d or, respectively, the diameter of the hard gelatin capsules 1.

The outer ring 25 is enclosed by protective covers 32 at least in the regions of the circumference thereof, whereat the hard gelatin capsules 1 would fall out of the guide grooves 27 due to the aforementioned geometry of the apertures 28. Hence, the hard gelatin capsules 1 are prevented from falling out of said guide grooves as a result of the gravitational force through the apertures 28 (FIG. 1).

In an embodiment of the invention, which is not depicted, it would also be conceivable for the apertures 28, as viewed in the direction of transportation, to have a width B such that said width is smaller than the thickness d or rather the diameter of the hard gelatin capsules 1; and therefore said hard gelatin capsules 1 can likewise be prevented from falling out of the apertures 28 strictly as a result thereof.

Along the conveying path of the hard gelatin capsules 1 in the conveyor wheel 15 (in the exemplary embodiment in the clockwise direction), said hard gelatin capsules 1 enter into the conical radiation area of a radiation source embodied as an X-ray source 30. As can particularly be seen with the aid of FIGS. 2 and 3, the radiation area 31 is configured or aligned in such a way that all of the hard gelatin capsules 1 which are situated in a group of apertures 28 that are in the region of the radiation area 31 are irradiated during a standstill phase of the conveyor wheel 15.

In a preferred but not restrictive manner, the X-ray source 30 or rather the radiation cone 33 thereof is aligned such that the center axis 34 of the radiation cone 33 runs perpendicularly to the longitudinal axis 2 of the hard gelatin capsules 1, i.e. such that said hard gelatin capsules 1 are irradiated in a plane that is perpendicular to the longitudinal axis 2.

At least one sensor element 35, which is embodied as an image recording sensor element 35 and is connected to an evaluation device 36, is disposed on the side of the hard gelatin capsules 1 opposite the radiation cone 1. An image of the irradiated hard gelatin capsule 1 is produced by means of the sensor element 35, and said image is supplied to the evaluation device. By means of an algorithm located in the evaluation device 36, said evaluation device 36 recognizes whether the irradiated hard gelatin capsules 1 have a certain required property, for example a certain filling weight or, for example, whether said capsules have any foreign particles. In consideration of the details of the evaluation of such images produced by sensor elements 35, reference is made in this regard to the German patent application DE 10 2010 038 544 A1 of the applicant, which in this respect is considered to be a constituent part of the present application.

In the exemplary embodiment depicted, the sensor element 35 is disposed radially within the inner ring 24, to which end the inner ring 24 consists of a material permeable to the radiation of the X-ray source 30, for example plastic, at least in the region of the radiation cone 33.

A removal device 40 comprising removal tabs 41 joins the X-ray source 30 along the subsequent conveying path of the conveyor wheel 15. Only one individual removal tab 41 is shown in the exemplary embodiment depicted. The device 10 comprises, however, a number of removal tabs 41 which correspond to the number of receiving shafts 19 and can be individually actuated. Hard gelatin capsules 1 transported into the respective apertures 28 can be removed via the removal tabs, in particular by means of a corresponding position of the ejector flap 41, or can, for example, be delivered via a slide 42 to an unspecified check weigher. The removal device 40 is preferably disposed in a lower region of the conveyor wheel 15 with respect to the conveyor wheel 15 wheel itself; thus enabling the hard gelatin capsules 1 to be removed from the apertures, for example, solely by means of gravity.

The device 10 described to this point operates as follows: During a standstill phase of the conveyor wheel 15, the desired number of hard gelatin capsules 1 are in each case brought from the receiving shafts 19 into the apertures 28 that are positioned in alignment with the outlets of the receiving shafts 19. The conveyor wheel 15 is subsequently conveyed in a stepped manner into the region of the radiation cone 33 of the radiation source 30, where an image of the irradiated hard gelatin capsules 1 is recorded using the sensor element 35.

The image is preferably only then captured if the outer ring 25 has been rotated back by a certain path value, for example 1 mm, against the direction of transportation of the hard gelatin capsules 1. In so doing, the hard gelatin capsules 1 are completely released from the apertures 28 of the outer ring; and therefore said outer ring 25 does not affect the image.

This image is delivered to the evaluation unit 36 and evaluated. Should it become evident that individual hard gelatin capsules 1 do not have the desired properties ("bad capsules"), these hard gelatin capsules 1 are then removed from the conveyor wheel 15 in the region of the removal device 40 by means of a corresponding positioning of the removal flap 41. In contrast thereto, hard gelatin capsules 1 which have the desired properties ("good capsules") are not removed or discharged but are delivered to a further processing location by positioning the ejector flap in a corresponding manner.

Figure 4:
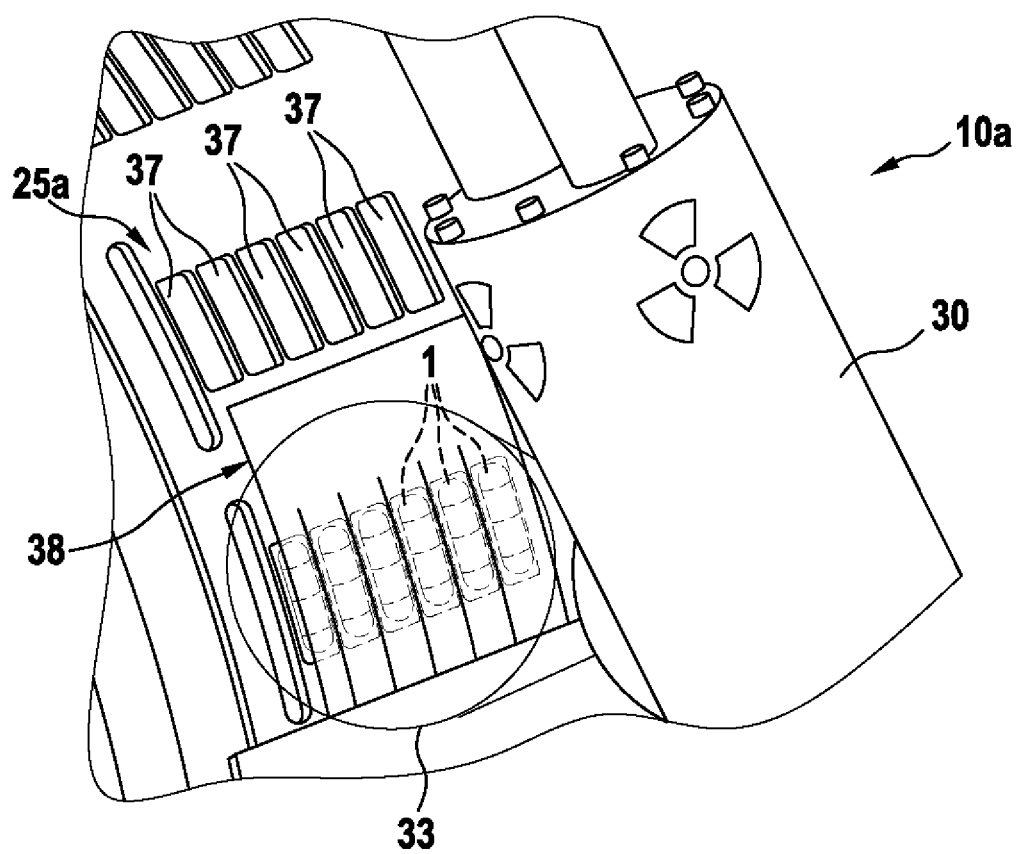
FIG. 4 shows a device modified with respect to the first device in the region of the X-ray source in a perspective view.

In FIG. 4, a device 10a which is modified with respect to FIGS. 1 to 3 is depicted. In contrast to the device 10, this device 10a does not have a stationary inner ring 24, but rather the outer ring 25a has receiving areas 37 for the hard gelatin capsules 1 which are analogous to the apertures 28 in the outer ring 25 and in which the hard gelatin capsules 1 are accommodated such that said capsules cannot move relative to another component (as in the case of the inner ring 24 of the device 10) during transport. A clamping plate 38 which is permeable to radiation and which pushes the hard gelatin capsules 1 against the bottom of the receiving areas 37 is furthermore disposed in the region of the X-ray source 30 or, respectively, the radiation cone 33. As a result, the hard gelatin capsules 1 are held tightly in the receiving areas 37 when the outer ring 25a is rotated backwards and are consequently released in the longitudinal direction of said receiving areas 37.

Figure 5:
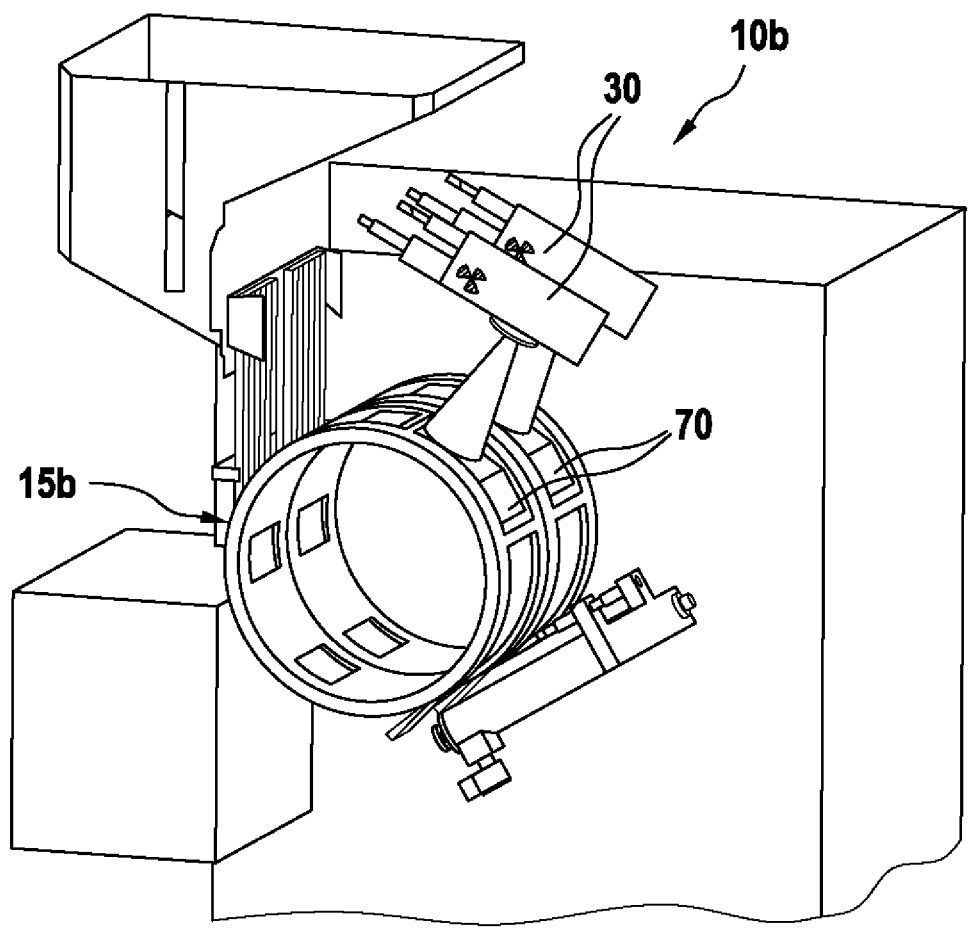
FIG. 5 shows a further modified device in a perspective view.

In the device 10b depicted in FIG. 5, the conveyor wheel 15b has receiving elements 70 that are exchangeably attached and are embodied as formatting portions for the hard gelatin capsules 1. Analogous to the receiving areas 37 of the device 10a shown in FIG. 4, receiving areas for the hard gelatin capsules are configured in the receiving elements 70. In addition, the device 10b has two X-ray sources 30 disposed parallel to one another for receiving elements 70 disposed parallel to one another in the direction of rotation.

Figure 6:
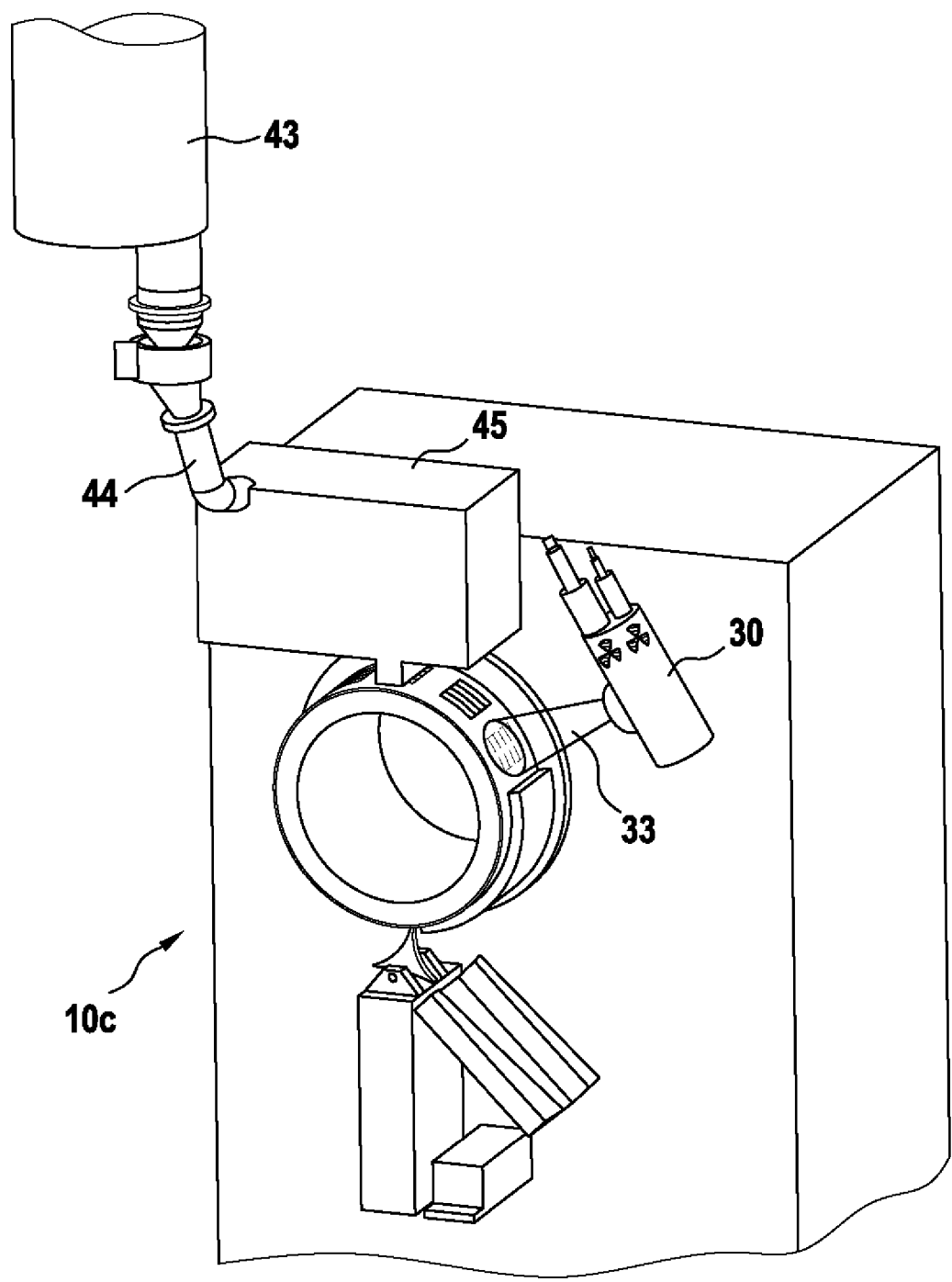
FIG. 6 shows a device modified with respect to FIG. 1 in the region of the device for feeding the products into the receiving areas of the conveyor wheel in a perspective view.

In FIG. 6, a further device 10c modified with respect to FIGS. 1 to 4 is depicted. The device 10c has a bulk storage unit in the form of a capsule storage container 43 that is connected to a format-independent feeding apparatus 45 via a feeding tube 44. The feeding apparatus 45, which is, for example, pneumatically driven, extracts hard gelatin capsules 1 from the tube 44, for example by means of vacuum or more precisely negative pressure and delivers the same to receiving areas 37 or, respectively, apertures 28 in the conveyor wheel 15.

Figure 7:
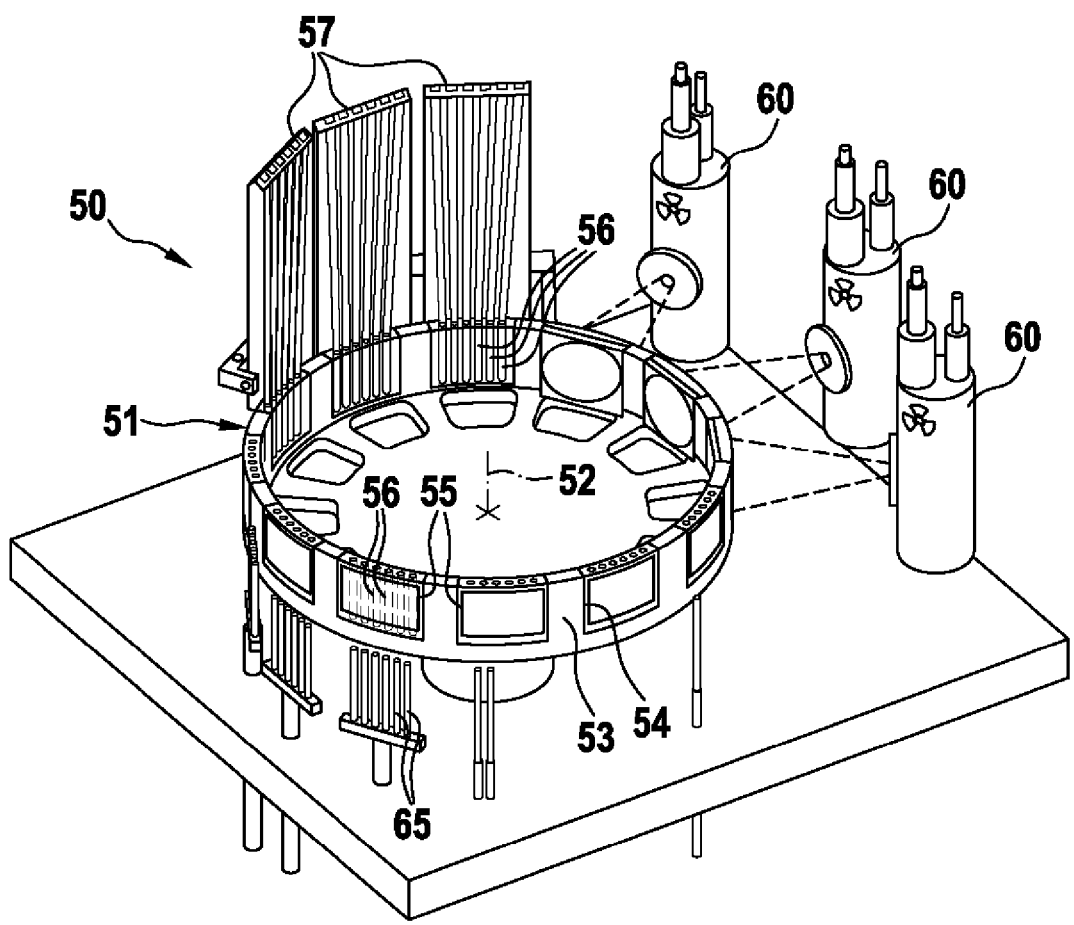
FIG. 7 shows a simplified, partially sectioned depiction of a second inventive device while using a conveyor wheel rotated about a vertical axis of rotation.

In FIG. 7, device 50 is depicted which again has been modified. In contrast to the devices 10, 10a, 10b, the device 50 comprises a conveyor wheel 51 which is rotated in a stepped manner about a vertically disposed axis of rotation 52. Receiving areas 54 for exchangeably attaching formatting portions 55 are configured so as to be spaced apart at uniform angular distances on an annular, vertically aligned outer wall 53 of the conveyor wheel 51.

A plurality of through-holes 56 is configured in each case in the formatting portions 55. Said through-holes are likewise preferably vertically aligned, serve as receiving areas for the hard gelatin capsules 1 and have in each case a height or rather a length which makes it possible to accommodate in each case a plurality of hard gelatin capsules 1 disposed vertically as a row one on top of the other in the through-holes 56. The formatting portions 55 consist of a material, in particular plastic that is permeable to X-rays. The through-holes 56 of the formatting portions 55 are filled with the hard gelatin capsules 1 via shaft-shaped feeding grooves 57 from an unspecified bulk storage unit, blocking devices 20 being disposed in each case in the region of the feeding grooves 57 corresponding to the device 10.

In the exemplary embodiment depicted, a plurality of X-ray sources 60 is disposed along the conveying path of the conveyor wheel 51 outside of the outer periphery thereof. The number of X-ray sources 60 preferably corresponds thereby to the number of feeding grooves 57. When, for example, three feeding grooves 57 are present, the conveyor wheel 51 can then in each case be further rotated in a stepped manner about an angle of rotation range which corresponds to the partitioning of the three feeding grooves 57.

In order to be able remove individual hard gelatin capsules 1 which have been recognized to be "bad" from the conveyor wheel 51 or more precisely from the through-holes of the formatting portions 55, discharge rams 65, which can be moved upwards and downwards in accordance with the double arrow 61, are provided along the conveying path of the conveyor wheel 51 that continues after the X-ray sources 60. Said discharge rams 65 can move into the through-holes 56, which are designed as stepped bores, of the formatting portions 55 in order to thereby remove the hard gelatin capsules 1 situated in the region of the through-hole 56.

The devices described to this point 10, 10a, 10b, 10c and 50 can be modified in a variety of ways without deviating from the concept of the invention. Said concept consists of the use of a conveyor wheel 15, 51 in which the hard gelatin capsules 1 or, respectively, pharmaceutical products are conveyed or rather disposed during the irradiation thereof by the X-ray source 30, 60. Particularly the feeding apparatuses for feeding the hard gelatin capsules 1 into the conveyor wheels 15, 51 can thus be designed differently. Provision can furthermore be made for the devices 10, 10*a*, 10*b*, 10*c*, and 50 to be equipped with check weighers for calibrating the evaluation device 36.

The invention claimed is:

1. A device for checking pharmaceutical products, by means of at least one radiation source, and a conveying device which conveys the products in a clocked manner in a radiation area of the radiation source, wherein radiation is captured on a side of the products opposite the radiation source by means of at least one sensor element which is coupled to an evaluation device, wherein the conveying device is embodied as a conveyor wheel which can rotate in a stepped manner about a vertically disposed axis, wherein the products are arranged, while being conveyed in the radiation area, in receiving areas of the conveyor wheel, wherein the receiving areas are embodied as vertically disposed receiving bores for the products and wherein the receiving bores are disposed in formatting portions that are exchangeably attached to the conveyor wheel, characterized in that the formatting portions comprise a material permeable to the radiation of the radiation source to facilitate imaging of the products within the receiving bores by the radiation source and the at least one sensor element, without vertically aligning the radiation source with the receiving bores.

2. The device according to claim 1, characterized in that each of the formatting portions has a plurality of receiving bores.

3. The device according to claim 1, characterized in that discharge rams for removing products from the receiving bores are provided along a conveying path of the conveyor wheel.

4. The device according to claim 1, characterized in that multiple products are vertically disposed on top of each other in each of the receiving bores.

5. The device according to claim 1, characterized in that the formatting portions are disposed on an annular, vertically aligned outer wall of the conveyor wheel so as to be spaced apart at uniform angular distances.

6. The device according to claim 1, characterized in that a plurality of X-ray sources is disposed along the conveying path of the conveyor wheel outside of the outer periphery thereof.

7. The device according to claim 6, characterized in that a center axis of a radiation cone of the X-ray sources of the products extends perpendicularly to a longitudinal axis of said products such that said products are irradiated in a plane perpendicular to the longitudinal axis thereof.

8. The device according to claim 1, characterized in that the products are irradiated within the conveyor wheel.

9. A device for checking pharmaceutical products, by means of at least one radiation source, and a conveying device which conveys the products in a clocked manner in a radiation area of the radiation source, wherein radiation is captured on a side of the products opposite the radiation source by means of at least one sensor element which is coupled to an evaluation device, wherein the conveying device is embodied as a conveyor wheel which can rotate in a stepped manner about an axis and wherein the products are arranged, while being conveyed in the radiation area, in receiving areas of the conveyor wheel, wherein the conveyor wheel has a stationary inner ring which forms a support surface for the products and is radially enclosed by an outer ring, wherein the receiving areas are configured in the outer ring, wherein the outer ring is rotationally mounted, wherein the axis of the conveyor wheel is disposed horizontally, wherein the conveyor wheel interacts with a removal device which is disposed in a region of said conveyor wheel, wherein the receiving areas have an extension in a direction of rotation of the outer ring, said extension being greater than an extension of the products within the receiving areas in the direction of transportation, wherein the radiation area of the radiation source embodied as a radiation cone is disposed in a region of the conveyor wheel in which the products are prevented from moving independently in the direction of transportation by a frictional force between the products and a receiving surface of the inner ring, and wherein the outer ring is rotated in and against the direction of transportation of the products.

10. The device according to claim 9, characterized in that the sensor element is disposed on a side of the inner ring facing away from the radiation source.

11. The device according to claim 9, characterized in that the inner ring has guide grooves for the products.

12. A device for checking pharmaceutical products, by means of at least one radiation source, and a conveying device which conveys the products in a clocked manner in a radiation area of the radiation source, wherein radiation is captured on a side of the products opposite the radiation source by means of at least one sensor element coupled to an evaluation device, wherein the conveying device is embodied as a conveyor wheel which can rotate in a stepped manner about an axis and wherein the products are arranged, while being conveyed in the radiation area, in receiving areas of the conveyor wheel, wherein the conveyor wheel has an outer ring comprising the receiving areas, wherein the axis of the conveyor wheel is disposed horizontally and wherein the products disposed in the receiving areas are fixed in said receiving areas in a region of the radiation source by means of a clamping element that is permeable to the radiation.

13. The device according to claim 12, characterized in that receiving elements for the products which are adapted to a format of said products are exchangeably attached to the conveyor wheel.

14. The device according to claim 9, characterized in that the outer ring is enclosed at least in regions by a protective cover at least in a region of the receiving areas, said protective cover preventing the products from falling out of the receiving areas during the rotational movement of the outer ring.

15. The device according to claim 9, characterized in that feeding of the products from a storage container, which accommodates said products in an irregular manner, into the receiving areas of the conveyor wheel takes place by means of a shaft-shaped, format-dependent feeding element.

16. The device according to claim 9, characterized in that feeding of the products from a storage container, which accommodates said products in an irregular manner, into the receiving areas of the conveyor wheel takes place by means of a format-independent feeding apparatus.

17. The device according to claim 1 wherein the pharmaceutical products are hard gelatin capsules.

18. The device according to claim 1 wherein the radiation source is an X-ray source.

19. The device according to claim 1 wherein the formatting portions are made of plastic.

20. The device according to claim 9 wherein the pharmaceutical products are hard gelatin capsules.

21. The device according to claim 9 wherein the radiation source is an X-ray source.

22. The device according to claim 9 wherein the receiving areas are apertures.

23. The device according to claim 9 wherein the products fall out of the receiving areas by means of gravity.

24. The device according to claim 12 wherein the pharmaceutical products are hard gelatin capsules.

25. The device according to claim 12 wherein the radiation source is an X-ray source.

* * * * *